(12) United States Patent
Adlassnig (10) Patent No.: US 9,938,555 B2
(45) Date of Patent: Apr. 10, 2018

(54) DETERMINATION OF HYDROGEN PEROXIDE CONCENTRATIONS

(76) Inventor: Alexander Adlassnig, Vienna (AT)

( * ) Notice: Subject to any disclaimer, the term of this patent is extended or adjusted under 35 U.S.C. 154(b) by 1360 days.

(21) Appl. No.: 12/441,716

(22) PCT Filed: Sep. 18, 2007

(86) PCT No.: PCT/EP2007/008121
§ 371 (c)(1),
(2), (4) Date: Oct. 9, 2009

(87) PCT Pub. No.: WO2008/034587
PCT Pub. Date: Mar. 27, 2008

(65) Prior Publication Data
US 2010/0258451 A1 Oct. 14, 2010

(30) Foreign Application Priority Data
Sep. 18, 2006 (DE) .................. 10 2006 043 718

(51) Int. Cl.
*C12Q 1/00* (2006.01)
*G01N 27/327* (2006.01)

(52) U.S. Cl.
CPC ......... *C12Q 1/006* (2013.01); *G01N 27/3273* (2013.01)

(58) Field of Classification Search
USPC .............................. 205/792, 782; 204/403.11
See application file for complete search history.

(56) References Cited

U.S. PATENT DOCUMENTS

| 3,791,988 A | 2/1974 | Josef et al. |
| 4,566,949 A | 1/1986 | Berger |
| 4,929,545 A | 5/1990 | Freitag |
| 5,206,147 A | 4/1993 | Hoenes |
| 5,234,516 A | 8/1993 | Okamura et al. |
| 5,288,636 A | 2/1994 | Pollmann et al. |
| 5,353,351 A | 10/1994 | Bartoli et al. |
| 5,385,846 A | 1/1995 | Kuhn et al. |
| 5,411,647 A * | 5/1995 | Johnson et al. ............ 205/777.5 |
| 5,858,799 A * | 1/1999 | Yee et al. ...................... 436/164 |

(Continued)

FOREIGN PATENT DOCUMENTS

| CN | 1615343 | 5/2005 |
| DE | 102 12 570 | 10/2003 |

(Continued)

OTHER PUBLICATIONS

Bisenberger, M., Brauchle, C., Hampp, N. "A triple step potential waveform at enzyme multisensors with thick0film gold electrodes for detection of glucose and sucrose." Sensor and Actuators B, col. 28, pp. 181-189, 1995.*

(Continued)

*Primary Examiner* — Louis J Rufo
(74) *Attorney, Agent, or Firm* — Klarquist Sparkman, LLP (57) ABSTRACT

For amperometric determination of the hydrogen peroxide concentration in a fluid sample, different electrical voltage steps are applied to the electrodes. In this process, at least one voltage is suitable for measuring the hydrogen peroxide concentration in the fluid sample, and at least one additional voltage is suitable for measuring the concentration of a substance in the fluid sample that acts as an interfering substance during measurement of the hydrogen peroxide concentration.

24 Claims, 4 Drawing Sheets

(56) References Cited

U.S. PATENT DOCUMENTS

| | | | |
|---|---|---|---|
| 6,503,381 B1 * | 1/2003 | Gotoh et al. | 204/403.14 |
| 7,081,195 B2 * | 7/2006 | Simpson et al. | 205/777.5 |
| 2004/0259264 A1 * | 12/2004 | Morita et al. | 436/149 |
| 2005/0183965 A1 | 8/2005 | Davies | |
| 2007/0272564 A1 * | 11/2007 | Huang | 205/792 |

FOREIGN PATENT DOCUMENTS

| | | |
|---|---|---|
| EP | 0190740 | 8/1986 |
| EP | 0330517 | 8/1989 |
| EP | 0354441 | 2/1990 |
| EP | 0496730 | 8/1992 |
| EP | 0741186 | 11/1996 |
| JP | 63 081259 A | 4/1988 |
| JP | 03 113360 A | 5/1991 |
| JP | 07 103939 A | 4/1995 |
| JP | 2006 105615 A | 4/2006 |
| WO | WO81/03546 | 12/1981 |
| WO | WO95/21934 A1 | 8/1995 |
| WO | WO03/060015 | 7/2003 |
| WO | WO2005/057173 A | 6/2005 |
| WO | WO 2008040998 A2 * | 4/2008 |

OTHER PUBLICATIONS

Gerlache M. et al., "Pulsed Electrochemical Detection of $H_2O_2$ on Gold," *Electrochimica Acta, Elsevier Science Publishers*, 43, 23:3467-3473 (Jul. 30, 1998).

Matos et al., "Flow-Injection System With Enzyme Reactor for Differential Amperometric Determination of Hydrogen Peroxide in Rainwater," *Analytica Chimica Acta*, 441:73-79 (2001).

* cited by examiner

DETERMINATION OF HYDROGEN PEROXIDE CONCENTRATIONS

CROSS REFERENCE TO RELATED APPLICATIONS

This is the U.S. National Stage of International Application No. PCT/EP2007/008121, filed Sep. 18, 2007, which in turn claims the benefit of German Patent Application No. DE-10 2006 043 718.7, filed Sep. 18, 2006. Both applications are incorporated herein by reference.

BACKGROUND OF THE INVENTION

Field of the Invention

The invention concerns a method and a device for determining hydrogen peroxide concentrations in fluids, in particular an improved determination of hydrogen peroxide concentrations in blood, sweat, urine, or milk.

The determination of substances, specifically in the presence of other substances—some of which are interfering substances—is important for many areas of application, especially in medical diagnostics. For example, determining glucose in the blood is critically important for the treatment of diabetes. Treatment promises to be especially successful when blood sugar is checked at regular intervals by the patient himself. To do this, the patient pricks his finger with a lancing device to obtain a drop of blood, which he applies to a disposable biosensor. The biosensor is located in a measurement device that performs the measurement and analysis. After 10 to 30 seconds, the display shows the blood sugar reading, which the patient uses for ongoing monitoring and/or precise insulin dosing. This necessitates an accurate blood sugar measurement. Occasional erroneous measurements can lead to acute complications such as coma. Repeated erroneous measurements cause a persistent unphysiologically high blood sugar level, which leads to blindness, amputations, kidney failure and myocardial infarction.

Prior Art

A number of methods are known for determining blood sugar levels. These methods generally fall into two categories: optical methods and electrochemical methods. In the case of optical methods, reflectance spectroscopy or absorption spectroscopy are used to detect the quantity of chromophores formed in the reaction with glucose in the blood. The intensity of the color change is proportional to the blood sugar content.

Electrochemical methods use amperometric or coulometric techniques to determine the blood sugar content. The application possibilities and, above all, the performance of electrochemical methods are limited by the multitude of interfering substances in the blood (urea, amino acids, ascorbic acid, medications, etc.), since these substances can also be converted at the electrodes, thus producing erroneously elevated readings. The same applies to other variables, such as hematocrit, for example, which also can differ from measurement to measurement. The hematocrit (HCT) is the percentage of red blood cells in whole blood (in volume %). Normal hematocrit is between 40 and 45 volume %. In the case of illness or in accident victims with high blood loss, the HCT can be between approximately 22 and 65 volume %. The extent to which this affects measurement of the blood sugar content is described in U.S. Pat. Nos. 5,234,516; 5,288,636; 5,353,351 and 5,385,846, for example.

As a result of the uncertain chemical and physiological composition of the blood or other body fluids, the measurement results from the electrochemical glucose determination using the conventional method show deviations of up to 20% from the actual glucose value.

Disposable electrochemical sensors generally consist of a substrate upon which are formed contacts, lines, and electrodes made of a conductive material. The reaction zones and the contacts to the measurement device are defined by the application of a nonconductive layer. The reaction zone is formed by the electrodes. In general, two electrodes are present, one of them serving as measurement electrode. The other electrode represents the reference electrode and counter electrode. The actual detection reaction takes place at the measurement electrode. For this purpose, an enzyme layer or enzyme membrane is applied either to this electrode or in front of it. The enzyme is used to react specifically with the glucose in the blood. The measurement electrode now measures the concentration of one or more reaction products of the enzyme reaction. The concentration of the reaction products is directly proportional to the substrate concentration as long as the activity of the enzyme is higher than the substrate concentration. In this way, the measurement electrode directly determines the glucose concentration in the blood.

A number of enzyme sensors for measuring glucose in blood or other fluids are described in the literature. Nearly all glucose sensors function according to the following reaction scheme:

$$O_2 + H_2O + \text{glucose} \xrightarrow{\text{glucose oxidase (GOD)}} \delta\text{-glucolactone} + H_2O_2 \quad (I)$$

The glucose determination can take place either through (1) the consumption of oxygen ($O_2$ electrodes), (2) the hydrogen peroxide formed ($H_2O_2$ electrodes), or (3) the rise in pH (pH electrodes). Glucose sensors based on changes in pH have the disadvantage that their measurement behavior is determined by the buffer capacity of the sample.

In the case of $O_2$ and $H_2O_2$ electrodes, the measured value is directly proportional to the glucose concentration over a range that is large to a greater or lesser extent. The measurement range is determined by the membrane's permeability to glucose and oxygen. High permeability of the membrane makes for high sensitivity, while low permeability reduces the sensitivity but extends the measurement range. At high glucose concentrations, the measurement range may be limited by insufficient enzyme activity. However, this circumstance can be kept in check through the use of excess enzyme. It is important to keep in mind here that autoinhibition can occur with large enzyme quantities, especially in the case of glucose oxidase.

Without a membrane, the measurement range is limited to a maximum of approximately 200 mg/dl by the transport rate of oxygen to the enzyme. But in diabetes treatment, blood sugar levels between 200 and 500 mg/dl are commonplace. To reach this value without sacrificing sensitivity owing to thick membranes, oxygen-independent glucose sensors were developed. In these sensors, molecules other than oxygen transport the electrons from the enzyme redox center to the electrode surface. These molecules are known as mediators M. The mechanism proceeds in accordance with the following scheme:

Such sensors are oxygen-independent to a certain degree, and even function in anaerobic environments.

In electrochemical glucose determination in a complex medium such as blood or urine, however, the problem arises that numerous other substances contained in the medium can influence the measured current. In the case of direct $H_2O_2$ detection at approximately +0.6 V (NHE), a great number of easily oxidized compounds are converted at the same time, which produces false elevated readings. For this reason, the mediators used generally have low redox potentials, which reduces the effect of interfering species on the measurement result. Examples of suitable mediators include benzoquinones and naphtoquinones (EP 0 190 740), substituted flavins, phenazines, phenothiazines, indophenols, substituted 1,4-benzoquinones and indamines (EP 0 330 517), N-oxides, nitroso compounds, hydroxylamines and oxines (EP 0 354 441), soluble ferricyanide/ferric compounds (EP 0 496 730) and phenazinium/phenoxazinium salts (U.S. Pat. No. 3,791,988).

Glucose sensors with mediators have disadvantages, however. All mediators are toxic, for example. The natural reaction of glucose oxidase with oxygen from the medium cannot be prevented, since the affinity of the redox center to $O_2$ is approximately 100 times greater than to $Fe(III)CN_6$, for example. Especially at low glucose concentrations this occurs to a greater degree, and produces measured values that are too low, since the $H_2O_2$ formed by the reaction with oxygen is not detected. Moreover, when such sensors are manufactured, it is necessary to ensure that the mediator remains in the oxidized state until the time of measurement. Each reduction, even only a partial reduction, results in an increased background current, since $M_{red}$ molecules are already present, which of course are also converted. It is known (EP 0 741 186) that mediators tend toward fast reduction, especially at high temperatures and high humidity. Naturally, this decreases the shelf life, and hence the application possibilities for using the sensors as disposable sensors.

Two-electrode systems or three-electrode systems may be used. In both systems, the working electrodes and counter electrodes are typically made of platinum, gold, carbon, or the like. The reference electrode is an Ag—AgCl electrode, a calomel electrode, or made of the same material as the working electrode.

The international patent application with publication number WO 81/03546 discloses a method for measuring the glucose concentration in which a voltage curve (lower limit: −1.0 to −0.6 V; upper limit: +0.7 to +1.1 V) is applied which has dwell times at certain points (especially those where glucose is converted) and at the reversal points. The charge is determined in specific regions. The dwell point and dwell times are chosen such that the charge is proportional to the glucose concentration, independent of interfering substances, primarily urea and amino acids. The regions in which integration is performed are characterized in that glucose always provides only a positive contribution to the total charge, while in contrast the interfering substances make both positive and negative contributions which are thus averaged out of the integration.

However, this method fails when concentrations of interfering substances are high at the same time as glucose concentrations are low.

In sum, then, a method for determining glucose in the blood is desired that works with $H_2O_2$ electrodes, needs no mediators, is relatively insensitive to hematocrit and temperature, in which $H_2O_2$ detection can take place at a lower voltage range, making it more insensitive to interfering species. At the same time, the sensors should be storable, so that they can be used as disposable sensors.

SUMMARY OF THE INVENTION

Consequently, it is an object of the present invention to improve the accuracy of amperometric determination of hydrogen peroxide concentrations in a fluid sample, especially in blood, sweat, urine, or milk, and in particular to further reduce or entirely exclude the influence of interfering substances on the results of the determination.

This object is attained by the method defined in claim 1, and by the devices defined in claims 22 and 23. Additional, improved embodiments of the invention are defined in the dependent claims.

One embodiment of the invention is a method for amperometric determination of the hydrogen peroxide concentration present in a fluid sample, particularly blood, serum, plasma, urine, interstitial fluid, sweat, or milk, with the aid of electrodes to which different voltages E are applied during a measurement cycle. The method comprises measurement at a voltage $E_M$ that is suitable for measuring the hydrogen peroxide concentration in the fluid sample, and measurement at least one voltage $E_K$ that is suitable for measuring the concentration of a substance in the fluid sample that acts as an interfering substance during measurement of the hydrogen peroxide concentration, particularly urea, amino acids, ascorbic acid, and certain medications.

The result or results of the additional measurement(s) at one or more voltage(s) $E_{Kn}$ that is/are suitable for measuring the concentration of an interfering substance in the fluid sample can be used to estimate the influence of this/these interfering substance(s) on the result of the measurement at the voltage that is suitable for measuring the hydrogen peroxide concentration in the fluid sample. This makes the result of the glucose determination insensitive to the influence of one or more interfering substance(s) that is/are contained in the fluid sample at unknown concentrations.

In order to measure the hydrogen peroxide concentration or the concentration of an interfering substance in the fluid sample, preferably a voltage is applied at which the current flowing between the electrodes changes essentially linearly, but at most exponentially, with the hydrogen peroxide concentration or with the interfering substance concentration.

According to a preferred embodiment of the invention, in order to estimate the influence of the interfering substances, the results of the measurements at voltages suitable for measuring the interfering substances, each multiplied by a weighting factor a empirically determined in advance, are subtracted from the result of the measurement at the voltage suitable for measuring the hydrogen peroxide concentration. The total current at the typical hydrogen peroxide voltage is corrected with the aid of the measured currents at various typical interfering substance voltages multiplied by a weighting factor, thus producing a more accurate value in a simple manner.

According to another preferred embodiment, the measurements at the different voltages are repeated, typically until a certain convergence criterion is reached. Inaccuracies due to measurement error or outliers can be compensated in this way.

In one embodiment, an activation voltage, which typically lies between −200 and +700 mV, preferably at 0 V, is applied prior to application of the first measurement voltage. As a result, the measurement voltage can be shifted far into the cathodic range.

Preferably a maximum of 10 different voltages are applied, and typically 4, which lie in the ranges of −1200 to −800 mV, −600 to 0 mV, −200 to +700 mV and +200 to +1400 mV. The measurement voltages applied for the purpose of determining the concentrations of the interfering substances generally are more cathodic than the measurement voltage $E_M$, so that little substrate is consumed.

In a typical application for the invention, for example in determining the glucose concentration in the fluid, the hydrogen peroxide is the end product of an enzyme reaction. Preferably at least one oxoreductase is used in the enzyme reaction, e.g., glucose oxidase in the case of glucose determination. Additional substrates can be determined by other suitable enzymes, such as, e.g., lactate oxidase, cholesterol oxidase, alcohol dehydrogenase, xanthine oxidase, amino acid oxidase, ascorbic acid oxidase, acyl-CoA oxidase, uricase, glutamate dehydrogenase, fructose dehydrogenase or the like.

According to a preferred embodiment of the invention, gold electrodes are used as the electrodes.

Additional preferred embodiments of the invention are measurement devices that can be used to carry out the above-described method. These measurement devices may have the measurement electrodes integrated, for example on a measurement chip, or else the measurement electrodes are applied to an external measurement strip that is electrically connected to the measurement device.

In the measurement devices, the electrochemical voltage drops in the fluid sample are preferably compensated through a control circuit.

Furthermore, in an advantageous embodiment of the measurement devices, the voltage of the measurement electrode is held at a constant value during the entire measurement by a control circuit.

BRIEF DESCRIPTION OF THE DRAWINGS

The above-described, and additional, objects, aspects and advantages of the invention may be better understood with the following detailed description of the preferred embodiments of the invention, in which reference is made to the drawings, in which.

DETAILED DESCRIPTION OF THE PREFERRED EMBODIMENTS OF THE INVENTION

According to the invention, multiple measurement voltage steps are applied to the electrodes of the sensor.

In this process, at least one voltage is chosen such that it is suitable for measuring the hydrogen peroxide concentration. In particular, this is a voltage in which the measured current is linear or, at most, exponential to the hydrogen peroxide concentration, which is to say that it changes linearly or at most exponentially with a change in the hydrogen peroxide concentration.

In addition, at least one voltage is chosen such that it is suitable for measuring the concentration of a substance that acts as an interfering substance during the above measurement of the hydrogen peroxide concentration, which is to say that influences the current flowing between the electrodes during the hydrogen peroxide measurement, in particular increases it. An additional measurement voltage of this nature thus makes it possible to estimate the concentration of a specific interfering substance and is, in particular, a voltage at which the measured current is linear with respect to the concentration of the interfering substance instead of being linear with respect to the hydrogen peroxide concentration.

The estimate(s) of the interfering substance(s) can then be used as a correction filter with regard to the preliminary estimate of the hydrogen peroxide concentration, in that the current that is contributed by the interfering substance(s) to the measurement at the voltage for hydrogen peroxide measurement is estimated, and the measured value is corrected accordingly. For example, if the measured value is the level of the measured current flowing at the voltage for the hydrogen peroxide measurement, then the estimated value of the quantity of the interfering substance determined according to the above process for this measured value can be subtracted from said measured value.

The following describes how the contribution of the interfering substances to the measured value at the voltage $E_M$ for determining the hydrogen peroxide concentration can be estimated from the measured values at the voltages $E_{K1}$ to $E_{Kn}$ for determining the interfering substance concentrations, and how the former measured value can be corrected for (final) determination of the hydrogen peroxide concentration.

In the case of blood sugar measurement, the actual measurable concentration at a typical voltage $E_{Ki}$ for measuring the interfering substance concentration is then determined using the process described above for the interfering substances k1, k2, . . . kn. This typical voltage is, for example, a voltage at which the measured current is linear to the concentration of the interfering substance. As measured values, one then obtains the current values $I_{k1}$, $I_{k2}$, . . . , $I_{kn}$. In addition, the preliminary value of the hydrogen peroxide concentration is determined using the above-described process at a typical voltage $E_M$ for measuring the hydrogen peroxide concentration, with the current value $I_M$ being obtained as the measured value.

The current value $I_{M'}$ is then calculated from these measured values using the following working equation:

$$I_{M'} = I_M - a_1 \cdot I_{k1} - a_2 \cdot I_{k2} - \ldots - a_n \cdot I_{kn} \qquad \text{(III)}$$

The constants $a_1, a_2, \ldots, a_n$ are weighting factors, which must be determined in advance in preliminary experiments in the laboratory. They are needed because $I_{k1}, I_{k2}, \ldots, I_{kn}$, as noted above, are measured at the voltages $E_{k1}, E_{k2}, \ldots$, $E_{kn}$, where the $E_k$ are different from the $E_M$, typically smaller. Moreover, in the case of multiple interfering substances, the relationship is no longer linear, since the substances influence one another. The relationship varies depending on the concentration of the interfering substances and the quantity of the additional components present. In sum, multiple factors enter into $a_i$.

The above working equation is programmed into the measurement device. It must be noted, however, that additional factors have some influence on the calculation of the blood sugar concentration, and may also supplement the above working formula. Such factors include, in particular, an estimate of the proportion of measured current brought about by the particular interfering substances whose concentrations are not measured separately using the above method. Moreover, in addition to the chemical composition of the fluid sample, physical and physiological properties, such as the temperature of the sample, can affect the measured currents.

The determination of blood glucose content will now be described using an example. This determination is accomplished through a reaction of the sample with glucose oxidase, forming hydrogen peroxide, and through amperometric determination of the quantity of hydrogen peroxide that was formed.

Figure 3:
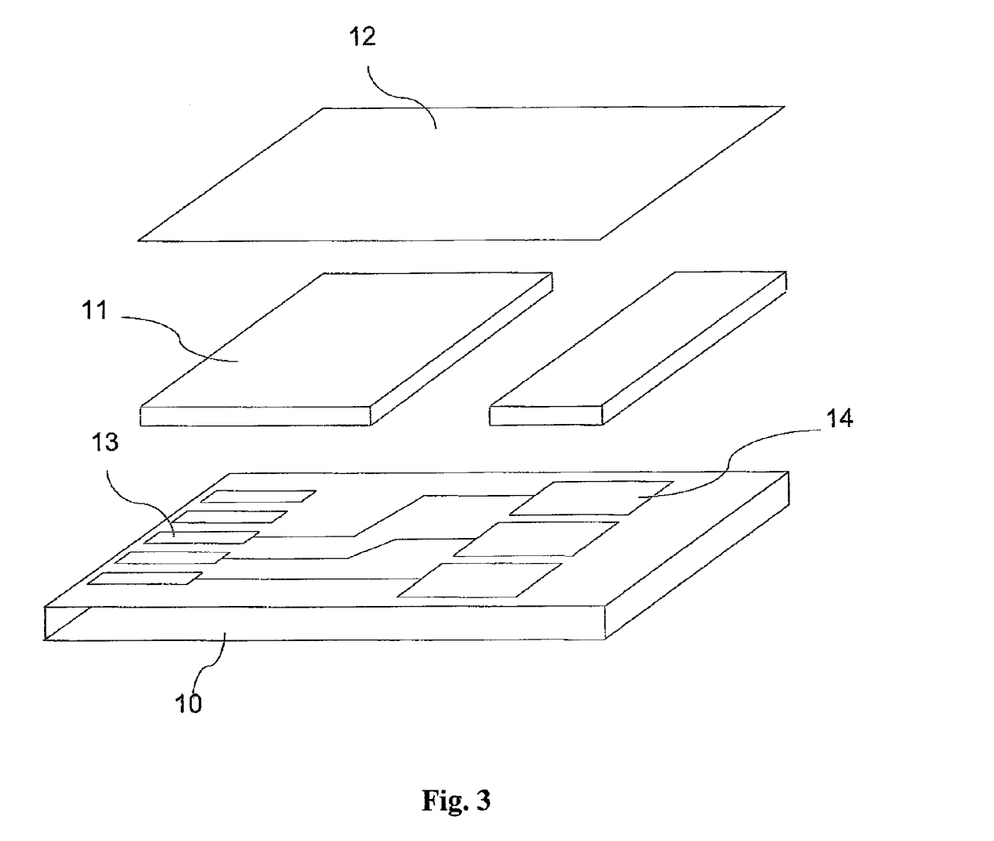
FIG. 3 shows the schematic structure of a test strip suitable for carrying out the measurement.
Figure 4:
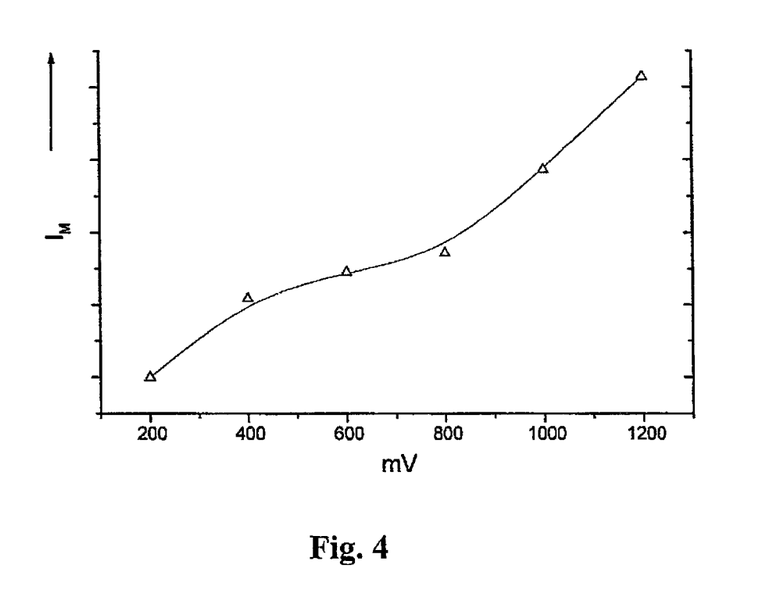
FIG. 4 shows the curve of the measured current $I_M$ at different hydrogen peroxide voltages $E_M$ for an example.
Figure 5:
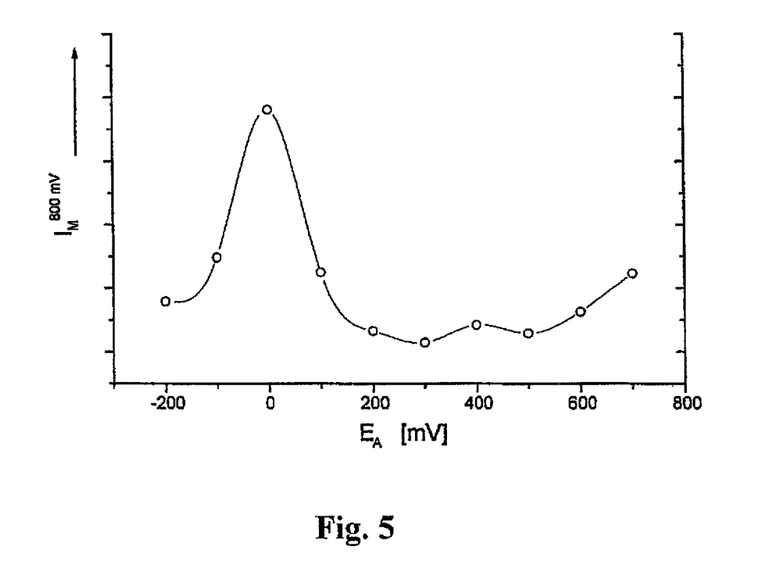
FIG. 5 shows the effect of the size of the activation voltage $E_A$ on the measured current for $E_M$=+800 mV for the example from FIG. 4.

To this end, at least two, preferably a maximum of ten, and typically four, voltages are applied to the measurement electrode of the test strip from FIG. 3. The measurement strip consists of three electrodes (14): measurement, counter, and reference electrode. The substrate 10 is made of a thermoplastic film (for example, PVC from Ineos, Germany). Above the electrode surfaces, a capillary is produced by a spacer film 1 (for example, Duplobond® from Lohmann, Germany) and a cover film 12 with hydrophilic coating (for example, Hostaphan® RN HSTE from Mitsubishi Polyester Films, Germany). The glucose oxidase is applied to the electrode surface using a screen printing process (for example, HEMA GX from Aurum Technology, Austria). Example voltage ranges for the typical case are:

$E_A$: −200 to +200 mV
$E_M$: +400 to +800 mV
$E_{k1}$: −400 to −600 mV
$E_{k2}$: −800 to −1000 mV.

$E_A$ is an activation voltage. The reason for this is as follows: it is known of gold electrodes that the oxidation of $H_2O_2$ takes place at two different voltages (M. Gerlache et al., Electrochimica Acta, Vol. 43, No. 23, pages 3467 to 3473, 1998). The first peak is in the region of the onset of oxide formation ($E_p$=+0.49 V), and the second—somewhat more anodic peak—is fully in the oxide region ($E_p$=+0.87 V). The height of the first peak, in particular, depends very much on the composition of the electrode and the composition of the medium. Formation of the first peak is accelerated by adsorbed OH ions at the gold surface. If no OH ions can be adsorbed (e.g., in the case of high Cl ion concentrations and/or surface-active substances in the medium, dirty or oxidized surface), the first peak either does not form at all or is very weak. However, this first peak in particular is well-suited for the detection of $H_2O_2$, since the half-wave potentials of $H_2O_2$ oxidation and of oxide formation are separate from one another. This permits more sensitive measurement than with platinum electrodes, for example, which always measure oxide formation together with $H_2O_2$ detection.

It has become evident that the measurement voltage can be shifted far into the cathodic range (to +0.1 V) by the application of a voltage below the onset of oxide formation (activation voltage $E_A$) ahead of the actual measurement voltage ($E_M$). This is because a small catalytic quantity of oxide is formed on the electrode surface by the application of the activation voltage. This has the result that then measurement voltage is reduced from at least +0.6 V (NHE) to below +0.4 V. As a result, the effect of interfering species on the measured current is also reduced, and the use of mediators is no longer absolutely necessary.

The working formula in the example now appears as follows:

$$I_{M'} = I_M - a_1 \cdot I_{k1} - a_2 \cdot I_{k2} \tag{IV}$$

The effectiveness of this method is evident when one compares the confidence intervals (CI) with and without the correction term. In the case of determining the blood glucose content through reaction of the sample with glucose oxidase, forming hydrogen peroxide and amperometric determination of the quantity of hydrogen peroxide that was formed using the method described, one obtains a confidence interval of 0.96999. When one includes the correction term with the empirically determined weighting factors $a_1$=−0.11 and $a_2$=047 in the equation, the confidence interval rises to 0.99922.

The blood sugar concentration G can then be derived directly from $I_{M'}$, since it is proportional to the hydrogen peroxide concentration, which in turn is proportional to $I_{M'}$ (in this case referred to as $I_{BZ}$). G is obtained with the intercept d and the slope k (both from the calibration) as follows:

$$G = \frac{I_{BZ} - d}{k} \tag{V}$$

All voltages refer to the internal reference electrode. The voltage that is suitable for measuring the hydrogen peroxide concentration is between +200 and +1400 mV. In the voltage range between +770 and +1030 mV, the confidence interval (with no correction term) is 95%.

Figure 1:
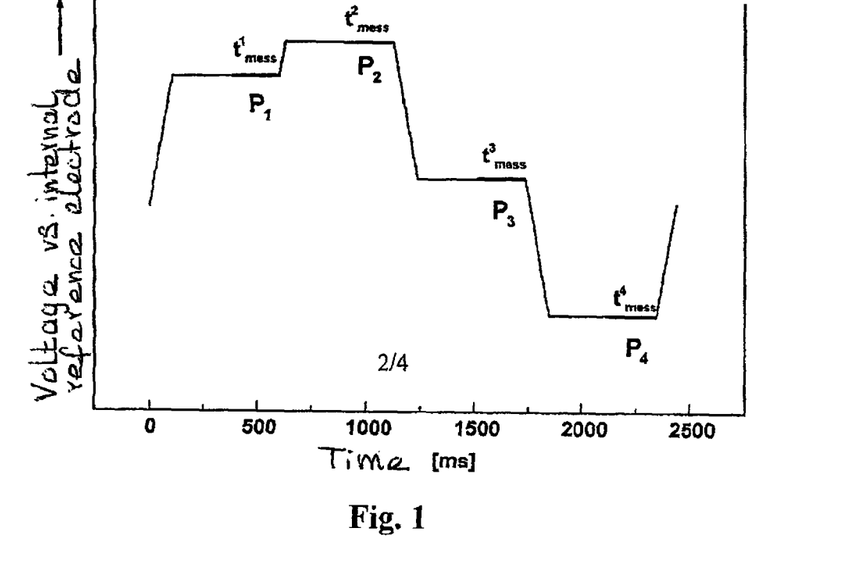
FIG. 1 shows a typical curve of a voltage applied to the measurement electrodes.

FIG. 1 shows an exemplary behavior of a curve of the voltage with four voltage steps $P_1$ through $P_4$ applied between the measurement electrodes. The largest anodic voltage—$P_2$ in FIG. 1—is typically the voltage that is suitable for measuring the hydrogen peroxide concentration. The voltage $P_1$ corresponds to the activation voltage $E_A$ for reducing the measurement voltage $E_M$ to <+0.6 V (NHE). Accordingly, $P_3$ and $P_4$ represent voltage steps that are suitable for measuring two different interfering parameters.

The four time spans $t^1_{mess}$ to $t^4_{mess}$ characterize the time periods during which measurements can be performed: $t^2_{mess}$ is the time span during which the measurement (or multiple pulsed measurements) can be carried out with respect to the hydrogen peroxide concentration; $t^3_{mess}$ and $t^4_{mess}$ are the time spans during which each of the measurements with respect to the interfering substances can be carried out. In iterative measurement, $t^1_{mess}$ only plays a role in the first cycle. Here it is used to verify whether the test strip is in order. In the subsequent cycles, no measurement is carried out at $P_1$.

Each of the measurement periods is located at the end of the time period in which a voltage step is applied.

Figure 2:
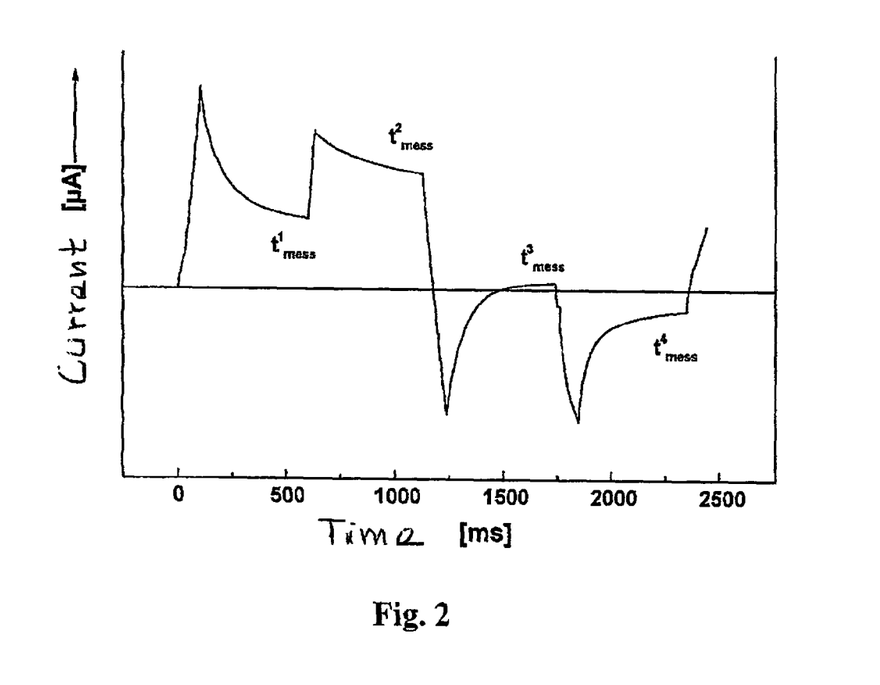
FIG. 2 shows a typical curve of the measured current in reaction to the voltage curve shown in FIG. 1.

FIG. 2 shows the current curve corresponding to the voltage curve from FIG. 1. The way the current between the measurement electrodes first becomes stable at the end of each time period in which a voltage is applied is clearly evident in FIG. 2. These ends correspond to the four measured time spans $t^1_{mess}$ to $t^4_{mess}$.

For determining the glucose concentration, the measurement voltage and the corresponding measurements preferably are run through repeatedly rather than just one time, as already mentioned above. When the blood sugar value G thus obtained no longer changes, the final value is shown on the display.

Figure 6:
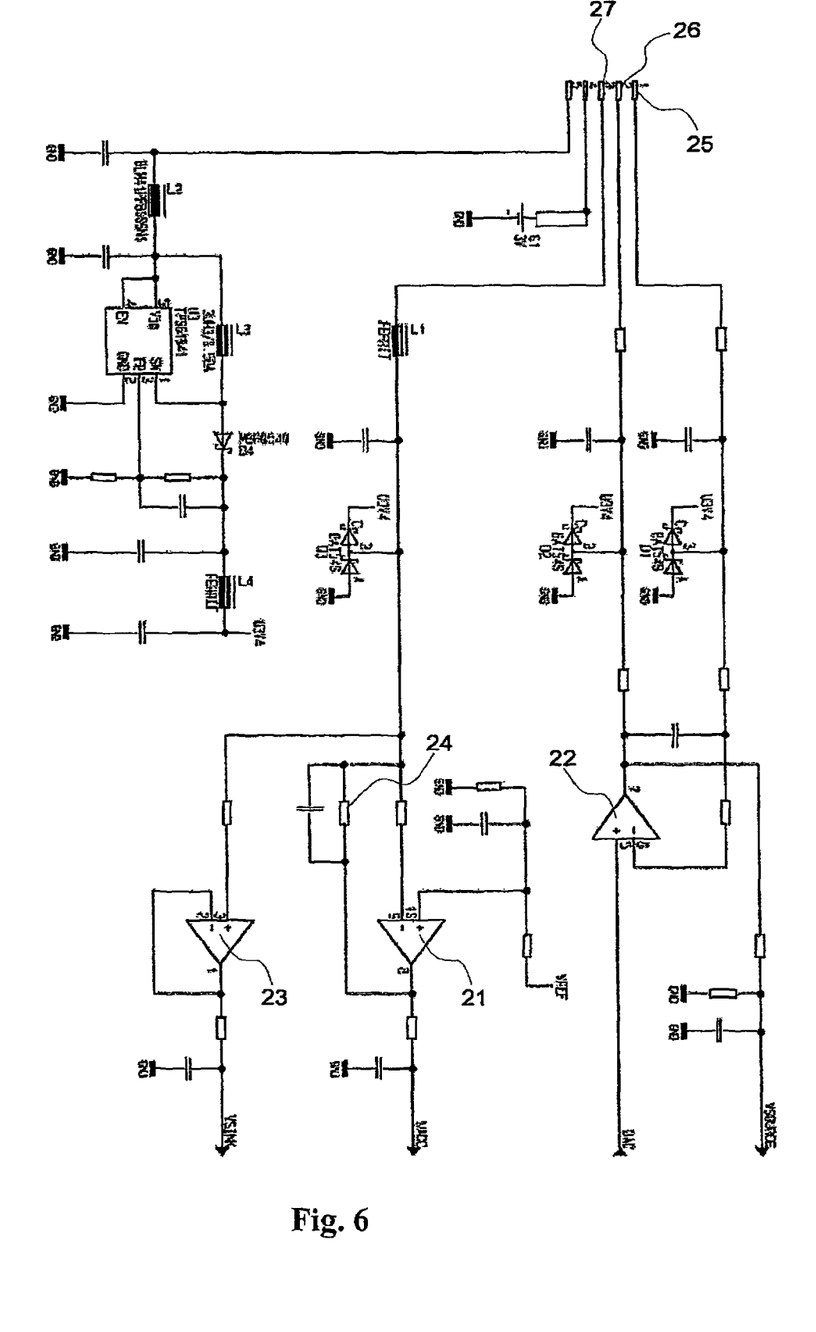
FIG. 6 shows a control circuit for impressing the voltage steps according to the invention.

The circuit for impressing the inventive voltage steps is shown in FIG. 6. The voltage of the measurement electrode is held at a constant value by the operational amplifier (OP) 21 (pins 5, 6, 7) through the contact 27. By means of a digital-to-analog converter (DAC; not shown) up to ten voltage steps of different height and length are generated and impressed on the regulator 22 (pins 8, 9, 10) as target values. The regulator 22 compensates electrochemical voltage drops in the blood during the measurement (IR compensation). The voltage between the measurement electrode and the reference electrode (with the measurement device connected through contact 25) thus follows the target value.

The electrode current flows through the measurement resistor $R_{Mess}$ (27) and produces a voltage drop there. The regulator 23 (pins 1, 2, 3), acting as a voltage follower, brings the voltage VSINK of the measurement electrode to the analog-to-digital converter (ADC; not shown), and the regulator 21 (pins 5, 6, 7) brings the voltage after the measurement resistor 24 ($U_{ADC}$). The current produced at the electrodes by the detection reaction is determined by the following formula:

$$I = \frac{U_{ADC} - VSINK}{R_{Mess}} \quad (VI)$$

What is claimed is:

1. Method for determining glucose concentration in a fluid sample, in which the fluid sample is brought into contact with glucose oxidase and an amount of hydrogen peroxide forming thereby is amperometrically measured with electrodes to which different potential steps are applied, the method comprising:
   applying an activation potential so as to form a catalytic quantity of oxide on an electrode surface for shifting a potential for the measurement of hydrogen peroxide concentration into a cathodic range;
   applying a first measurement potential different than the activation potential that is suitable for measuring the hydrogen peroxide concentration in the fluid sample and which was shifted into the cathodic range by previously applying the activation potential, and measurement at the first measurement potential;
   applying at least a second measurement potential at which the current between the electrodes is nonlinear with respect to the hydrogen peroxide concentration but that is suitable for measuring a concentration of a substance in the fluid sample that acts as an interfering substance during measurement of the hydrogen peroxide concentration, and measurement at the second measurement potential; and
   estimating, based on the measurement at the second measurement potential an influence of the interfering substance on the result of the measurement at the first measurement potential.

2. Method according to claim 1, characterized in that, at the first measurement potential, the current flowing between the electrodes changes at most exponentially with the hydrogen peroxide concentration.

3. Method according to claim 2, characterized in that, at the first measurement potential, the current flowing between the electrodes changes essentially linearly with the hydrogen peroxide concentration.

4. Method according to claim 3, characterized in that, at the second measurement potential, the current flowing between the electrodes changes at most exponentially with the interfering substance concentration.

5. Method according to claim 4, characterized in that, at the second measurement potential, the current flowing between the electrodes changes essentially linearly with the interfering substance concentration.

6. Method according to claim 1, characterized in that, in order to estimate the influence of the interfering substances, the result of the measurement at potentials suitable for measuring the hydrogen peroxide concentration is corrected with the results of the measurements at the potentials suitable for measuring the interfering substances, each multiplied by a predetermined weighting factor.

7. Method according to claim 6, characterized in that the measurement result is a current value.

8. Method according to claim 1, characterized in that the measurements at the different potentials are carried out multiple times.

9. Method according to claim 1, characterized in that the activation potential lies between −200 and +700 mV.

10. Method according to claim 9, characterized in that the activation potential is 0 V.

11. Method according to claim 1, characterized in that a maximum of 10 different potentials are applied.

12. Method according to claim 11, characterized in that precisely four different potentials are applied.

13. Method according to claim 12, characterized in that a first potential lies in a range of −1200 to −800 mV, a second potential lies in a range of −600 to 0 mV, a third potential lies in a range of −200 to +700 mV and a fourth potential lies in a range of +200 to +1400 mV.

14. Method according to claim 1, characterized in that the fluid sample is blood, sweat, urine, or milk.

15. Method according to claim 1, characterized in that the interfering substances are urea, amino acids, ascorbic acid, or medications.

16. Method according to claim 1, characterized in that the hydrogen peroxide is the end product of an enzyme reaction.

17. Method according to claim 16, characterized in that at least one oxoreductase is used in the enzyme reaction.

18. Method according to claim 17, characterized in that the oxoreductase that is used is glucose oxidase, lactate oxidase, cholesterol oxidase, alcohol dehydrogenase, xanthine oxidase, amino acid oxidase, ascorbic acid oxidase, acyl-CoA oxidase, uricase, glutamate dehydrogenase, or fructose dehydrogenase.

19. Method according to claim 1, characterized in that the electrodes are gold electrodes.

20. Measurement device, comprising:
   two or more electrodes;
   a control circuit adapted to:
      apply an activation potential so as to form a small catalytic quantity of oxide on the electrode surface to shift the potential for the measurement of the hydrogen peroxide concentration into a cathodic range;
      applying a first measurement potential, different than the activation potential and that is suitable for measuring the hydrogen peroxide concentration in the fluid sample and which was shifted into the cathodic range by previously applying the activation potential;

applying at least a second measurement potential at which the current between the electrodes is nonlinear with respect to the hydrogen peroxide concentration but that is suitable for measuring the concentration of a substance in the fluid sample that acts as an interfering substance during measurement of the hydrogen peroxide concentration; and wherein the measurement device is adapted to estimate, with the aid of the result of the measurement at the second measurement potential, the influence of the interfering substance on the result of the measurement at the first measurement potential.

21. Measurement device that can be connected to a measurement strip which has two or more electrodes, comprising:

a control circuit configured to:

apply an activation potential, so as to form a small catalytic quantity of oxide on the electrode surface, for shifting the potential for the measurement of the hydrogen peroxide concentration into the cathodic range;

apply a first measurement potential, different than the activation potential and that is suitable for measuring the hydrogen peroxide concentration in the fluid sample and which was shifted into a cathodic range by previously applying the activation potential;

apply at least a second measurement potential at which the current between the electrodes is nonlinear with respect to the hydrogen peroxide concentration but that is suitable for measuring the concentration of a substance in the fluid sample that acts as an interfering substance during measurement of the hydrogen peroxide concentration; and wherein the measurement device is adapted to estimate, with the aid of the result of the measurement at the potential that is suitable for measuring the concentration of the interfering substance, the influence of this interfering substance on the result of the measurement at the potential that is suitable for measuring the hydrogen peroxide concentration in the fluid sample.

22. Measurement device according to claim 20, characterized in that the control circuit is configured to compensate electrochemical potential drops in the fluid sample.

23. Measurement device according to claim 20, characterized in that the control circuit is configured to hold a potential of the measurement electrode at a constant value during the entire measurement.

24. Method according to claim 1, wherein the first measurement potential is applied and the measurement at the first measurement potential is performed with the catalytic quantity of oxide on the electrode surface.

* * * * *